(12) United States Patent
Oshodi et al.

(10) Patent No.: US 11,970,724 B2
(45) Date of Patent: Apr. 30, 2024

(54) SERUM-FREE CELL CULTURE MEDIUM

(71) Applicant: Regeneron Pharmaceuticals, Inc., Tarrytown, NY (US)

(72) Inventors: Shadia Abike Oshodi, Jersey City, NJ (US); Amy S. Johnson, Briarcliff Manor, NY (US); Shawn M. Lawrence, Nyack, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 17/370,389

(22) Filed: Jul. 8, 2021

(65) Prior Publication Data

US 2021/0332402 A1  Oct. 28, 2021

Related U.S. Application Data

(63) Continuation of application No. 16/742,695, filed on Jan. 14, 2020, now Pat. No. 11,332,771, which is a continuation of application No. 14/211,245, filed on Mar. 14, 2014, now abandoned.

(60) Provisional application No. 61/790,136, filed on Mar. 15, 2013.

(51) Int. Cl.
| | | |
|---|---|---|
| *C12P 21/00* | (2006.01) | |
| *C07K 16/18* | (2006.01) | |
| *C12N 5/00* | (2006.01) | |
| *C12N 5/071* | (2010.01) | |

(52) U.S. Cl.
CPC ............. *C12P 21/00* (2013.01); *C07K 16/18* (2013.01); *C12N 5/0031* (2013.01); *C12N 5/0037* (2013.01); *C12N 5/0043* (2013.01); *C12N 5/005* (2013.01); *C12N 5/0682* (2013.01); *C12N 2500/22* (2013.01); *C12N 2500/24* (2013.01); *C12N 2500/32* (2013.01); *C12N 2500/34* (2013.01); *C12N 2500/46* (2013.01); *C12N 2510/02* (2013.01); *C12N 2511/00* (2013.01)

(58) Field of Classification Search
CPC ....... C12P 21/00; C07K 16/18; C12N 5/0031; C12N 5/0037; C12N 5/0043; C12N 2500/32; C12N 2500/46; C12N 2510/02; C12N 2511/00
See application file for complete search history.

(56) References Cited

U.S. PATENT DOCUMENTS

| | | |
|---|---|---|
| 4,072,565 A | 2/1978 | Weiss et al. |
| RE30,985 E | 6/1982 | Cartaya et al. |
| 4,560,655 A | 12/1985 | Baker |
| 4,615,977 A | 10/1986 | Hasegawa et al. |
| 4,657,866 A | 4/1987 | Kumar |
| 4,786,599 A | 11/1988 | Chessebeuf et al. |
| 5,063,157 A | 11/1991 | Stockinger |
| 5,122,469 A | 6/1992 | Mather et al. |
| 5,342,777 A | 8/1994 | Cole et al. |
| 5,426,699 A | 6/1995 | Wunderlich et al. |
| 5,529,920 A | 6/1996 | Cole et al. |
| 5,610,279 A | 3/1997 | Brockhaus et al. |
| 5,705,364 A | 1/1998 | Etcheverry et al. |
| 5,811,299 A | 9/1998 | Renner et al. |
| 5,856,179 A | 1/1999 | Chen et al. |
| 5,976,833 A | 11/1999 | Furukawa et al. |
| 6,043,092 A | 3/2000 | Block |
| 6,048,728 A | 4/2000 | Inlow et al. |
| 6,087,123 A | 7/2000 | Wissler et al. |
| 6,146,847 A | 11/2000 | Goffe et al. |
| 6,180,401 B1 | 1/2001 | Chen et al. |
| 6,528,286 B1 | 3/2003 | Ryll |
| 6,589,759 B1 | 7/2003 | Loscalzo et al. |
| 6,924,124 B1 | 8/2005 | Singh |
| 6,927,004 B2 | 8/2005 | Eurlings et al. |
| 7,070,959 B1 | 7/2006 | Papadopoulos et al. |
| 7,087,411 B2 | 8/2006 | Daly et al. |
| 7,105,348 B2 | 9/2006 | Murphy et al. |
| 7,279,159 B2 | 10/2007 | Daly et al. |
| 7,294,484 B2 | 11/2007 | Drapeau et al. |
| 7,303,694 B2 | 12/2007 | Murphy et al. |
| 7,429,491 B2 | 9/2008 | Luan et al. |
| 7,435,553 B2 | 10/2008 | Fandl et al. |
| 7,455,988 B2 | 11/2008 | Fandl et al. |
| 7,582,298 B2 | 9/2009 | Stevens et al. |
| 7,666,416 B2 | 2/2010 | Etcheverry et al. |

(Continued)

FOREIGN PATENT DOCUMENTS

| | | |
|---|---|---|
| CN | 1241573 A | 1/2000 |
| CN | 1367258 A | 9/2002 |

(Continued)

OTHER PUBLICATIONS

Allen et al., "Inhibition of Lymphocyte Proliferation by Polyamines Requires Ruminant-Plasma Polyamine Oxidase," Eur. J. Biochem. 102, 153-158 (1979).

(Continued)

*Primary Examiner* — David W Berke-Schlessel
*Assistant Examiner* — Trent R Clarke
(74) *Attorney, Agent, or Firm* — Kramer Levin Natftalis & Frankel LLP; Jonathan S. Caplan

(57) ABSTRACT

The specification describes an improved serum-free animal cell culture medium, which can used for the production of a protein of interest. Ornithine, or a combination of ornithine and putrescine can be added to serum-free media or chemically defined media to improve viable cell density, to reduce cell doubling time, and to increase the production of a protein of interest.

6 Claims, No Drawings

(56) References Cited

U.S. PATENT DOCUMENTS

| | | |
|---|---|---|
| 7,750,138 B2 | 7/2010 | Fang et al. |
| 7,771,997 B2 | 8/2010 | Chen et al. |
| 7,879,984 B2 | 2/2011 | Martin et al. |
| 7,951,577 B2 | 5/2011 | Murphy et al. |
| 8,021,881 B2 | 9/2011 | Reiter et al. |
| 8,043,617 B2 | 10/2011 | Stevens et al. |
| 8,062,640 B2 | 11/2011 | Sleeman et al. |
| 8,216,575 B2 | 7/2012 | Yu |
| 8,313,926 B2 | 11/2012 | Grillberger et al. |
| 8,440,408 B2 | 5/2013 | Grillberger et al. |
| 8,637,312 B2 | 1/2014 | Kruger et al. |
| 8,735,095 B2 | 5/2014 | Martin et al. |
| 8,871,209 B2 | 10/2014 | Stitt et al. |
| 8,945,559 B2 | 2/2015 | Dix et al. |
| 9,018,356 B2 | 4/2015 | Sleeman et al. |
| 9,045,536 B2 | 6/2015 | Merchant et al. |
| 9,079,948 B2 | 7/2015 | Orengo et al. |
| 9,127,265 B2 | 9/2015 | Grillberger et al. |
| 9,150,645 B2 | 10/2015 | Subramanian et al. |
| 9,173,880 B2 | 11/2015 | Dix et al. |
| 9,181,572 B2 | 11/2015 | Subramanian et al. |
| 9,217,168 B2 | 12/2015 | Prentice |
| 9,228,014 B2 | 1/2016 | Classon et al. |
| 9,260,515 B2 | 2/2016 | Stitt et al. |
| 9,265,827 B2 | 2/2016 | Wiegand et al. |
| 9,266,949 B2 | 2/2016 | Ramasubramanyan et al. |
| 9,302,015 B2 | 4/2016 | Papadopoulos et al. |
| 9,353,176 B2 | 5/2016 | MacDonald et al. |
| 9,359,434 B2 | 6/2016 | Subramanian et al. |
| 9,402,898 B2 | 8/2016 | Walsh et al. |
| 9,447,431 B2 | 9/2016 | Thess et al. |
| 9,499,616 B2 | 11/2016 | Subramanian et al. |
| 9,644,181 B2 | 5/2017 | Matsuyama et al. |
| 9,663,810 B2 | 5/2017 | Prentice |
| 9,714,411 B2 | 7/2017 | Grillberger et al. |
| 9,758,568 B2 | 9/2017 | Grillberger et al. |
| 9,809,796 B2 | 11/2017 | Grillberger et al. |
| 10,927,342 B2 | 2/2021 | Johnson et al. |
| 11,332,771 B2 | 5/2022 | Oshodi et al. |
| 2006/0094104 A1 | 5/2006 | Grillberger et al. |
| 2006/0094113 A1 | 5/2006 | Epstein et al. |
| 2007/0212770 A1 | 9/2007 | Grillberger et al. |
| 2007/0212778 A1 | 9/2007 | Bramke et al. |
| 2009/0137416 A1 | 5/2009 | Fandl et al. |
| 2009/0162901 A1 | 6/2009 | Chen et al. |
| 2010/0120093 A1 | 5/2010 | Von Fircks et al. |
| 2010/0227819 A1 | 9/2010 | Hernandez et al. |
| 2010/0285533 A1 | 11/2010 | Krueger et al. |
| 2010/0304436 A1 | 12/2010 | Chen et al. |
| 2010/0331527 A1 | 12/2010 | Davis et al. |
| 2011/0229933 A1 | 9/2011 | Krishnan et al. |
| 2012/0034674 A1 | 2/2012 | Grillberger et al. |
| 2012/0264170 A1 | 10/2012 | Merchant et al. |
| 2012/0308549 A1 | 12/2012 | Fogh et al. |
| 2013/0084605 A1 | 4/2013 | Zhou et al. |
| 2013/0130316 A1 | 5/2013 | Joosten et al. |
| 2013/0224855 A1 | 8/2013 | Gupta et al. |
| 2013/0295613 A1 | 11/2013 | Kishishita et al. |
| 2013/0344535 A1 | 12/2013 | Mundt et al. |
| 2014/0044730 A1 | 2/2014 | Yancopoulos et al. |
| 2014/0088295 A1 | 3/2014 | Smith et al. |
| 2014/0154726 A1 | 6/2014 | Yang et al. |
| 2014/0271642 A1 | 9/2014 | Murphy et al. |
| 2014/0271653 A1 | 9/2014 | Gurnett-Bander et al. |
| 2014/0271658 A1 | 9/2014 | Murphy et al. |
| 2014/0271681 A1 | 9/2014 | Martin et al. |
| 2014/0273095 A1 | 9/2014 | Oshodi et al. |
| 2015/0104867 A1* | 4/2015 | Grillberger .......... C12N 5/0043 435/358 |
| 2015/0203579 A1 | 7/2015 | Papadopoulos et al. |
| 2015/0203580 A1 | 7/2015 | Papadopoulos et al. |
| 2015/0216795 A1 | 8/2015 | Assadourian et al. |
| 2015/0259423 A1 | 9/2015 | Kirshner et al. |
| 2015/0266966 A1 | 9/2015 | Smith et al. |
| 2015/0313194 A1 | 11/2015 | Hu et al. |
| 2015/0337029 A1 | 11/2015 | Kyratsous et al. |
| 2015/0337045 A1 | 11/2015 | Okamoto et al. |
| 2016/0002594 A1 | 1/2016 | Yang et al. |
| 2016/0017029 A1 | 1/2016 | Walsh et al. |
| 2016/0024502 A1 | 1/2016 | Streicher et al. |
| 2016/0075778 A1 | 3/2016 | Okamoto et al. |
| 2016/0076068 A1 | 3/2016 | Engel et al. |
| 2016/0083689 A1 | 3/2016 | Grillberger et al. |
| 2016/0215040 A1 | 7/2016 | Kyratsous et al. |
| 2016/0237400 A1 | 8/2016 | Xian |
| 2016/0333385 A1 | 11/2016 | Kang et al. |
| 2017/0107553 A1 | 4/2017 | Kottakota et al. |
| 2017/0305999 A1 | 10/2017 | Leber et al. |
| 2018/0223249 A1 | 8/2018 | Johnson et al. |
| 2018/0298078 A1 | 10/2018 | Park et al. |
| 2018/0346881 A1 | 12/2018 | Clemens et al. |
| 2019/0010531 A1 | 1/2019 | Chen et al. |
| 2019/0092836 A1 | 3/2019 | Leister et al. |
| 2020/0131554 A1 | 4/2020 | Chen et al. |
| 2020/0149081 A1 | 5/2020 | Oshodi et al. |
| 2020/0157492 A1 | 5/2020 | Johnson et al. |
| 2020/0255880 A1 | 8/2020 | Chen et al. |
| 2021/0340560 A1 | 11/2021 | Clarke |
| 2021/0388407 A1 | 12/2021 | Chen et al. |
| 2021/0388408 A1 | 12/2021 | Chen et al. |
| 2022/0228187 A1 | 7/2022 | Oshodi et al. |

FOREIGN PATENT DOCUMENTS

| | | |
|---|---|---|
| CN | 101065480 A | 10/2007 |
| CN | 101220347 A | 7/2008 |
| CN | 101360820 A | 2/2009 |
| CN | 101603026 A | 12/2009 |
| CN | 102224239 A | 10/2011 |
| CN | 102317440 A | 1/2012 |
| EP | 1321515 | 6/2003 |
| EP | 2971040 B1 | 9/2018 |
| JP | 2013-208104 A | 10/2013 |
| WO | WO 99/035255 A2 | 7/1999 |
| WO | WO 00/75319 A1 | 12/2000 |
| WO | WO-02069733 A1 | 9/2002 |
| WO | WO 2005/028626 A2 | 3/2005 |
| WO | WO 2007/077217 A2 | 7/2007 |
| WO | WO 2008/063892 A2 | 5/2008 |
| WO | WO 2008/154014 A2 | 12/2008 |
| WO | WO 2011/079004 A1 | 6/2011 |
| WO | WO 2012/091124 A1 | 7/2012 |
| WO | WO 2014/020160 A1 | 2/2014 |
| WO | WO 2015/105609 A1 | 7/2015 |
| WO | WO-2015184009 A1 | 12/2015 |
| WO | WO 2019/010191 A1 | 1/2019 |

OTHER PUBLICATIONS

Altamirano et al., "Analysis of CHO Cells Metabolic Redistribution in a Glutamate-Based Defined Medium in Continuous Culture," Biotechnol. Prog., Nov.-Dec. 2001, 17(6), pp. 1032-1041.

Ashkenazi et al., "Protection against endotoxic shock by a tumor necrosis factor receptor immunoadhesin," PNAS USA, Dec. 1991, 88:10535-10539.

Bettger et al., "Rapid clonal growth and serial passage of human diploid fibroblasts in a lipid-enriched synthetic medium supplemented with epidermal growth factor, insulin, and dexamethasone," Proc. Natl. Acad. Sci. USA, 1981, 78(9), pp. 5588-5592.

Bokati et al., "Corrosion inhibition of copper, mild steel and galvanically coupled coppermild steel in artificial sea water in presence of 1H-benzotriazole, sodium molybdate and sodium phosphate," Corrosion Science (2017) 126:272-285.

Branca et al., "Inhibition of Ornithine Decarboxylase of HeLa Cells by Diamines and Polyamines," Biochem. J. (1980) 186, 925-931.

Brasel et al., "Hematologic Effects of flt3 Ligand In Vivo in Mice," Blood, 1996, 88(6), pp. 2004-2012.

Byrn et al., "Biological properties of a CD4 immunoadhesin," Nature (1990) 344:667-670.

Davidson et al., "The Nucleoprotein Content of Fibroblasts Growing in vitro," Biochem. J., 1945, 39(2), pp. 188-199.

(56) References Cited

OTHER PUBLICATIONS

Dulbecco et al., "Production of Plaques in Monolayer Tissue Cultures by Single Particulars of an Animal Virus," Proc. Natl. Acad. Sci. USA, 1952, 38(8), pp. 747-752.
Eagle et al., "Nutrition Needs of Mammalian Cells in Tissue Culture," Science, 1955, 122(3168), pp. 501-504.
Experimental report—Impact of Ornithine and Putrescine Addition on MB02 Culture, submitted by the opponent on Jul. 16, 2020 in Opposition Against European Patent No. 2970876, 9 pages.
Extract from Mosby's Medical Dictionary, 8th Edition, 2009: 1161-1162.
Extended European Search Report for European Application No. 18172141.6, dated Jun. 29, 2018, 11 pages.
Franěk et al., "Plant Protein Hydrolysates: Preparation of Defined Peptide Fractions Promoting Growth and Production in Animal Cells Cultures," Biotechnol. Prog. 16 (5):688-92 (2000).
Froud et al., "Polyamine enhanced product expression from transformed and recombinant cell lines,"Production of Biologicals from Animal Cells in Culture (Editors: Spier et al.), Butterworth-Heinemann Ltd, Oxford, 1991, pp. 107-109.
Fusi et al., "Effects of putrescine, cadaverine, spermine, spermidine, and β-phenylethylamine on cultured bovine mammary epithelial cells," Ital. J. Anim. Sci., vol. 7, 131-140, 2008.
Gahl et al., "Reversal by aminoguanidine of the inhibition of proliferation of human fibroblasts by spermidine and spermine," Chem.—Biol Interactions, 22 (1978) 91-98.
Google® Scholar search, "a trap molecule" pp. 1-2; Jul. 23, 2020.
Guirard et al., "Effect of polyamine structure on growth stimulation and spermine and spermidine content of lactic acid bacteria," Journal of Bacteriology, vol. 88, No. 1, p. 72-80, Jul. 1964.
Gupta, A.J., "Correlating composition and functionality of soy protein hydrolysates used in animal cell cultures," PhD thesis, Wageningen University, NL (2015), ISBN: 978-94-6257-320-8, pp. 1-127.
Ham, "Clonal Growth of Mammalian Cells in a Chemically Defined, Synthetic Medium," Nat'l Acad. Sci. USA, 1965, 53, pp. 288-293.
Han et al., "Effects of polyamines on apoptosis induced by simulated ischemia/reperfusion injury in cultured neonatal rat cardiomyocytes," Cell Biology International 31 (2007) 1345-1352.
Hawel, L. et al., "Selective putrescine export is regulated by insulin and ornithine in Reuber H35 hepatoma cells," Biochimica et Biophysica Acta, vol. 1222, No. 1, pp. 15-26, May 1994.
Hollenbaugh et al., "Construction of Immunoglobulin Fusion Proteins," Current Protocols in Immunology (2002), Supplement 48, Unit 10.19A, pp. 10.19A.1-10.19A.11.
Holliger et al., ""Diabodies": small bivalent and bispecific antibody fragments," PNAS USA, Jul. 1993, 90:6444-6448.
Holmes et al., "Serum Fractionation and the Effects of Bovine Serum Fractions on Human Cells Grown in a Chemically Defined Medium," Biochem. Cytol., 1961, 10, pp. 389-401.
Holtta, E. et al., "Polyamine dependence of Chinese hamster ovary cells in serum-free culture is due to deficient arginase activity," Biochimica et Biophysica Acta, vol. 721, No. 4, pp. 321-327, Dec. 1982.
Huang et al., "Maximizing Productivity of CHO Cell-Based Fed-Batch Culture Using Chemically Defined Media Conditions and Typical Manufacturing Equipment," Biotechnol. Prog., Sep.-Oct. 2010, 26(5), pp. 1400-1410.
Igarashi, K. et al., "Modulation of cellular function by polyamines," International Journal of Biochemistry and Cell Biology, vol. 42, No. 1, pp. 39-51, Jan. 2010.
International Search Report and Written Opinion of the International Search Authority for International Application No. PCT/US18/40734, dated Oct. 18, 2018, 18 pages.
Jensen et al., "Selective inhibition of fibroblasts by spermine in primary cultures of normal human skin epithelial cells," In Vitro, vol. 18, No. 10, Oct. 1982, pp. 867-871.
Kanemura et al., "In Vitro Screening of Exogenous Factors for Human Neural Stem/Progenitor Cell Proliferation Using Measurement of Total ATP Content in Viable Cells," Cell Transplantation, 2005, vol. 14, pp. 673-682.
Kang et al., "Metabolic markers associated with high mannose glycan levels of therapeutic recombinant monoclonal antibodies," Journal of Biotechnology (2015) 203: 22-31.
Kaufman, "Use of Recombinant DNA Technology for Engineering Mammalian Cells to Produce Proteins," Bioprocess Technology, 1990, vol. 10, pp. 15-69.
Kaufman et al., "Synthesis, Processing, and Secretion of Recombinant Human Factor VIII Expressed in Mammalian Cells," J. Biol. Chem., 1988, 263(13), pp. 6352-6362.
Kaufman, "Selection and Coamplification of Heterologous Genes in Mammalian Cells," Meth Enzymol, 1990, 185, pp. 537-566.
Kipriyanov et al., "Recombinant single-chain Fv fragments carrying C-terminal cysteine residues: Production of bivalent and biotinylated miniantibodies," Mol. Immunol. (1994) 31:1047-1058.
Kipriyanov et al., "Single-chain antibody streptavidin fusions: tetrameric bifunctional scFv-complexes with biotin binding activity and enhanced affinity to antigen," Human Antibodies and Hybridomas (1995) 6:93-101.
Lalonde et al., "Therapeutic glycoprotein production in mammalian cells," Journal of Biotechnology 251 (2017) 128-140.
Li and Wen, "Screening soy hydrolysates for the production of a recombinant therapeutic protein in commercial cell line by combined approach of near-infrared spectroscopy and chemometrics," Appl Microbiol Biotechnol (2013) 97:2653-2660.
McKinnon et al., "Expression, purification and characterization of secreted recombinant human insulin-like growth factor I (IGF-1) and the potent variant des (1-3) IGF-1 in Chinese hamster ovary cells," J. Mol. Endocrinol., 1991, 6, pp. 231-239.
Michael, A.J., "Biosynthesis of polyamines and polyamine containing molecules," Biochem. J. (2016) 473, 2315-2329.
Moore and Stein, "A Modified Ninhydrin Reagent for the Photometric Determination of Amino Acids and Related Compounds," J. Biol. Chem. 1954, vol. 211, pp. 907-913.
Moore et al., "Culture of Normal Human Leukocytes," J. Amer. Med. Assoc., 1967, 199(8), pp. 519-524.
Morrison and Seidel, "Cell spreading and the regulation of ornithine decarboxylase," Journal of Cell Science (1995) 108: 3787-3794.
Nagae et al., "Function and 3D Structure of the N-Glycans on Glycoproteins," Int. J Mol. Sci. 2012, 13, 8398-8429.
Nemkov et al., "Three-minute method for amino acid analysis by UHPLC and high-resolution quadrupole orbitrap mass spectrometry," Amino Acids, 2015, 47(11):2345-2357, 23 pages provided.
Office Action for Chinese Application No. 201480023485.4, dated Apr. 18, 2017.
Ornithine, Wikipedia, 3 pages, retrieved from https://en.wikipedia.org/wiki/Ornithine on May 11, 2020.
Orr et al., "Survival of Animal Tissue Cells in Primary Culture in the Absence of Serum," Appl. Microbiol., 1973, 25(1), pp. 49-54.
Pastorian et al., "Tolerance to Putrescine Toxicity in Chinese Hamster Ovary Cells is Associated with Altered Uptake and Export," Experimental Cell Research, 231, 284-295 (1997).
Pegg, "Regulation of Ornithine Decarboxylase," J. of Biol. Chem., May 2006, 281:21, pp. 14529-14532.
Pegg, "Toxicity of Polyamines and Their Metabolic Products," Chemical Research in Toxicology, 2013, 26, 1782-1800.
Poljak, RJ, "Production and structure of diabodies," Structure, Dec. 1994, 2:1121-1123.
Putrescine, Wikipedia, 5 pages, retrieved from https://en.wikipedia.org/wiki/Putrescine on May 11, 2020.
Raafay et al., "Aflibercept: a Potent Vascular Endothelial Growth Factor Antagonist for Neovascular Age-Related Macular Degeneration and Other Retinal Vascular Diseases," Biol Ther, 2012, 2:3, 22 pages.
Rasmussen et al., "Isolation, characterization and recombinant protein expression in Veggie-CHO: a serum-free CHO host cell line," Cytotechnology, 1998, 28: 31-42.

(56) References Cited

OTHER PUBLICATIONS

Richardson et al., "Metabolomics Analysis of Soy Hydrolysates for the Identification of Productivity Markers of Mammalia Cells for Manufacturing Therapeutic Proteins," Biotechnol. Prog., 2015, 31:522-531.
Ritacco et al., "Cell Culture Media for Recombinant Protein Expression in Chinese Hamster Ovary (CHO) Cells: History, Key Components, and Optimization Strategies," Biotechnol Prog., 2018, vol. 34, No. 6, pp. 1407-1426.
Rodrigues et al., "Comparison of commercial serum-free media for CHO-K1 cell growth and monoclonal antibody production," International Journal of Pharmaceutics (2012) 437: 303-305.
Rohrer et al., "Profiling N-linked oligosaccharides from IgG by high-performance anion-exchange chromatography with pulsed amperometric detection," Glycobiology, 2016, vol. 26, No. 6, 582-591.
Sarilumab, Wikipedia, 3 pages, downloaded May 25, 2020, retrieved from https://en.wikipedia.org/wiki/Sarilumab.
Shantz and Levin, "Regulation of ornithine decarboxylase during oncogenic transformation: mechanisms and therapeutic potential," Amino Acids (2007) 33: 213-223.
Sigma-Aldrich, "Ethylenediaminetetraacetic acid tetrasodium salt dihydrate," downloaded May 26, 2020, 3 pages, retrieved from https://www.sigmaaldrich.com/catalog/product/sigma/e6511?lang=en&region=US.
Sigma-Aldrich, "Nutrient Mixture F-12 Ham Formulation," Jan. 18, 2009, 7 pages, retrieved from https://www.sigmaaldrich.com/life-science/cell-culture/learning-center/media-formulations/f-12-ham.html on Apr. 12, 2019.
Stoner et al., "Putrescine stimulates growth of human bronchial epithelial cells in primary culture," In Vitro, 1980, 16(5):399-406.
Taylor et al., "A transgenic mouse that expresses a diversity of human sequence heavy and light chain immunoglobulins," Nucl. Acids Res., (1992) 20(23):6287-6295.
Declerck and Tebbey, "Importance of manufacturing consistency of the glycosylated monoclonal antibody adalimumab (Humira®) and potential impact on the clinical use of biosimilars," Generics and Biosimilars Initiative Journal (2016) 5:2, pp. 70-73.
ThermoFisher Scientific, Technical Resources, 11320, DMEM/F-12, [online], Retrieved from the Internet: <URL: http://www.thermofisher.com/us/en/home/technical-resources/media-formulation.55.html>, Retrieved from the Internet on Jan. 29, 2018, 3 pages.
Tobias et al., "Exposure to Ornithine Results in Excessive Accumulation of Putrescine and Apoptotic Cell Death in Ornithine Decarboxylase Overproducing Mouse Myeloma Cells," Cell Growth & Differentiation, Oct. 1995, vol. 6, 1279-1285.
Tome et al., "Excess putrescine accumulation inhibits the formation of modified eukaryotic initiation factor 5A (eIF-5A) and induces apoptosis," Biochem. J., (1997) 328, 847-854.
Urlaub et al., "Isolation of Chinese hamster cell mutants deficient in dihydrofolate reductase activity," Proc. Natl. Acad. Sci. USA, 1980, 77(7), pp. 4216-4220.
Wahl and Holzgrabe, "Amino acid analysis for pharmacopoeial purposes," Talanta, Jul. 2016, 154:150-163.
Ward et al., "Binding activities of a repertoire of single immunoglobulin variable domains secreted from *Escherichia coli*," Nature (1989) 341:544-546.
Williams et al., "Isolation and Long-Term Cell Culture of Epithelial-Like Cells From Rat Liver," Exp. Cell. Res., 1971, 69, pp. 106-112.
Wood et al., "High Level Synthesis of Immunoglobulins in Chinese Hamster Ovary Cells," J. Immuno., 1990, 145(9), pp. 3011-3016.
Casero, Jr. and Marton, "Targeting polyamine metabolism and function in cancer and other hyperproliferative diseases," Nature Reviews Drug Discovery, May 2007, vol. 6, pp. 373-390.
Kim et al., "Development of serum-free medium supplemented with hydrolysates for the production of therapeutic antibodies in CHO cell cultures using design of experiments," Applied Microbiology and Biotechnology, 2009, vol. 83, pp. 639-648.
Kou et al., "Increasing the productivity of TNFR-Fc in GS-CHO cells at reduced culture temperatures," Biotechnology and Bioprocess Engineering, 2011, vol. 16, pp. 136-143.
Kucharzewska et al., "Ornithine decarboxylase and extracellular polyamines regulate microvascular sprouting and actin cytoskeleton dynamics in endothelial cells," Experimental Cell Research (2010) 316: 2683-2691.
Kumar et al., "Differential protein expression following low temperature culture of suspension CHO-K1 cells," BMC Biotechnology, 2008, 8:42, 13 pages.
Matsuoka et al., "Improvement of production rate on recombinant CHO cells in two-stage culture," BMC Proceedings, 2013, 7(Suppl 6):p. 50, 2 pages.
Oguchi et al., "pH Condition in temperature shift cultivation enhances cell longevity and specific hMab productivity in CHO culture," Cytotechnology, 2006, 52: 199-207.
Purwaha et al., "Targeted metabolomic analysis of amino acid response to L-asparaginase in adherent cells," Metabolomics (2014) 10:909-919.
Shi et al., "A High-throughput Automated Platform for the Development of Manufacturing Cell Lines for Protein Therapeutics," Journal of Visualized Experiments, Sep. 2011, 55, e3010, 5 pages.
Borys et al., "Effects of Culture Conditions on N-Glycolylneuraminic Acid (Neu5Gc) content of a recombinant fusion protein produced in CHO cells," Biotechnology and Bioengineering, 2010, vol. 105: 1048-1057.

\* cited by examiner

SERUM-FREE CELL CULTURE MEDIUM

CROSS REFERENCE TO RELATED APPLICATIONS

This application is a continuation of U.S. patent application Ser. No. 16/742,695, filed Jan. 14, 2020, which is a continuation of U.S. patent application Ser. No. 14/211,245, filed Mar. 14, 2014, which claims priority to and the benefit of U.S. Provisional Patent Application No. 61/790,136, filed Mar. 15, 2013, the contents of each of which are herein incorporated by reference in their entireties.

FIELD

The invention relates to media for the culturing of cells and for the production of recombinant proteins. The invention specifically relates to serum-free media for the culturing of recombinant CHO cells for the production of protein biotherapeutics.

BACKGROUND

Cell culture media comprising serum or protein hydrolysate components (i.e., peptones and tryptones) have a long history of use in the production of recombinant proteins from cultured cells. These components contain growth factors and a wide variety of other uncharacterized elements beneficial to cell growth and culture. However, they also contain uncharacterized elements that reduce growth or otherwise negatively impact recombinant protein production. They can also be an unwelcome potential source of variability. Despite their drawbacks, the benefits of using sera and hydrolysates have outweighed some of the disadvantages and they have been widely used in many cell culture applications.

Human biological therapeutics (biopharmaceuticals) are generally produced in mammalian cell culture, particularly CHO cell culture. The presence of uncharacterized or partly characterized components in those cell cultures are highly undesirable for the manufacture of biopharmaceuticals for human use. The use of such uncharacterized or partly characterized components not only introduces production and regulatory inconsistencies, it raises the possibility of viral or fungal infection of the production culture.

The reduction of lot-to-lot variability in drug product yield and composition is another important factor in selecting a culturing process. Sera, hydrolysates, and other undefined elements introduce variability in the yield, composition, and quality of biopharmaceutical production lots. The quality and purity of media elements may also affect yield, since drug titers often rely in part on maintaining a particular balance of nutrients. Where the relative amounts of nutrients vary from one media lot to another, drug yield can vary and this variance can be unacceptable or uneconomical.

Using serum containing or hydrolysate-based media introduces downstream processing challenges. The concentration of a desired biopharmaceutical in culture is generally on the order of grams per liter. The presence of serum and hydrolysates in media can add more than 10 g/L of uncharacterized peptides and proteins, which must be removed in subsequent processing steps. Serum and hydrolysates can also introduce variability in the amount of metals and other trace elements in the media. The elimination of serum and hydrolysates from culture media therefore eliminates these variations and potential encumbrances to the production and processing of drug substance.

Among others, the benefits to using serum-free and hydrolysate-free media include reduction in cost, reduction in variablity between drug lots, and minimization of the risk of introducing adventitious agents from undefined and unrefined components. Furthermore, where media are defined and uniform between batch runs, qualifying runs to test new media batches against current media are likewise minimized. Thus, there is a need in the art for media for culturing mammalian cells, wherein the media are chemically-defined and free of sera and hydrolysates, or that are serum-free and contain low manageable levels of hydrolysates, and yet allow for healthy and robust cell growth and maintenance, and high-titer production of biopharmaceutical drug substance.

SUMMARY

The inventors have made the surprising discovery that the inclusion of ornithine, either with or without putrescine, in cell culture media that is free of sera ("OS" media) increases cell viability and density, reduces cell doubling time, and permits high titer protein production by those cells. The inventors have also discovered that OS media that contains low or trace amounts of protein hydrolysates or is chemically defined (i.e., contains no protein hydrolysates) in particular provides restored cell viability and density, cell doubling time, and high titer protein production.

In one aspect, the invention provides a cell culture medium, which is serum-free and comprises at least 0.09 mM±0.014 mM ornithine. In one embodiment the ornithine is present in the medium at a concentration ranging from 0.09±0.014 mM to 0.9±0.14 mM, such as 0.09±0.014 mM, 0.3±0.05 mM, 0.6±0.09 mM, or 0.9±0.14 mM ornithine. In some embodiments, the medium also contains at least 0.20±0.03 mM putrescine. In some embodiments, the additional putrescine is at a concentration ranging from 0.20±0.03 mM to 0.714±0.11 mM, such as 0.20±0.03 mM, 0.35±0.06, or 0.714±0.11 mM putrescine. In some embodiments, the medium contains 7.5 g/L hydrolysate. In some embodiments, the medium is free of any hydrolysate.

In one embodiment, the medium contains a base medium that is chemically defined, such as a custom formulation or a commercially available base medium. In one embodiment, the complete medium is chemically defined, free of sera and free of hydrolysate.

In some embodiments, the medium, which is at its useful concentration (i.e., 1×) contains at least 40±6 mM or at least 70±10.5 mM of a mixture of amino acids or amino acid salts. In one embodiment, the medium contains at least 40 mM of a mixture of amino acids. In this or another embodiment, the medium contains at least 70 mM of a mixture of amino acids. In one embodiment, the mixture of amino acids (with the notable exception of glutamine, which may be added back to the medium as a point of use addition) contains alanine, arginine, asparagine, aspartic acid, cysteine, glutamic acid, glycine, histidine, isoleucine, leucine, lysine, methionine, phenylalanine, proline, serine, threonine, tryptophan, tyrosine, and valine.

In some embodiments, the medium contains one or more fatty acids. In one particular embodiment, the medium contains a mixture of fatty acids (or fatty acid derivatives) and alpha tocopherol. Fatty acids or fatty acid derivatives are selected from the group consisting of linoleic acid, linolenic acid, thioctic acid, oleic acid, palmitic acid, stearic acid, arachidic acid, acid, lauric acid, behenic acid, decanoic acid, dodecanoic acid, hexanoic acid, lignoceric acid, myristic acid, and octanoic acid.

In some embodiments, the medium contains a mixture of nucleosides. In one embodiment, the medium contains adenosine, guanosine, cytidine, uridine, thymidine, and hypoxanthine.

In some embodiments, the medium contains a mixture of salts. Salts include divalent cations, such as calcium and magnesium. In one embodiment, the medium contains calcium chloride and magnesium sulfate. Other salts may include those of phosphate.

In a specific embodiment, the medium (1) contains 7.5 g/L of a hydrolysate, (2) is serum-free, (3) contains 0.09±0.014 mM, 0.3±0.05 mM, 0.6±0.09 mM, or 0.9±0.14 mM ornithine, (4) optionally additionally contains 0.20±0.03 mM, 0.35±0.06, or 0.714±0.11 mM putrescine, (5) contains at least about 40 mM or at least about 70 mM of a mixture of amino acids including alanine, arginine, asparagine, aspartic acid, cysteine, glutamic acid, glycine, histidine, isoleucine, leucine, lysine, methionine, phenylalanine, proline, serine, threonine, tryptophan, tyrosine, and valine, (6) contains tocopherol and a mixture of fatty acids, (7) contains a mixture of nucleosides including adenosine, guanosine, cytidine, uridine, thymidine, and hypoxanthine, and (8) contains salts of calcium, magnesium, and phosphate.

In another aspect, the invention provides a method for cultivating cells in a cell culture medium, such as any embodiment of the medium described in the foregoing aspect. In one embodiment, the method employs the steps of propagating or maintaining a cell or cells in a medium that (1) contains 7.5 g/L hydrolysate, or no hydrolysate, (2) is free of sera, (3) contains ornithine at a concentration of at least 0.09 mM±0.014 mM, (4) and optionally contains putrescine, such as at least 0.20±0.03 mM.

In some embodiments, the cell or cells are mammalian cells, avian cells, insect cells, yeast cells, or bacteria cells. In one embodiment, the cells are mammalian cells useful in the production of recombinant proteins, such as CHO cells or the derivative CHO-K1. In some embodiments, the cells express a protein of interest, such as a biotherapeutic protein. The biotherapeutic protein may be an antigen binding protein, which may contain an Fc domain. In some embodiments, the protein of interest is a receptor-Fc-fusion protein, such as an ScFv molecule or a trap molecule. Trap molecules include the VEGF trap and IL-1 Trap proteins. In some embodiments, the protein of interest is an antibody, such as a humanized monoclonal antibody, a bispecific antibody, or an antibody fragment.

Given the positive effects on cell growth by including ornithine or a combination of ornithine and putrescine in serum-free media, the cells cultured according to this method have an average doubling time that is no more than 30 hours. In one embodiment, the cell doubling time is no more than 24 hours. In one embodiment, when compared to cell growth in media that contains less than 0.09±0.014 mM ornithine (or less than 0.09±0.014 mM ornithine and less than 0.2±0.03 mM putrescine), the cells grown according to this method have an average doubling time that is at least one third the doubling time of the comparator control culture.

Likewise, the inclusion of ornithine alone ora combination of ornithine and putrescine in serum-free media allows cultured cells to reach a higher viable cell count density than without the inclusion of ornithine or the combination of ornithine and putrescine. In one serum-free and hydrolysate-free embodiment of the OS medium, the cell culture is capable of attaining a viable cell count density that is at least 15% greater than a similar cell culture in a similar cell culture medium that contains less than 0.09±0.014 mM ornithine (or less than 0.09±0.014 mM ornithine and less than 0.2±0.03 mM putrescine). In another serum-free and hydrolysate-free embodiment of the OS medium, the cell culture is capable of attaining a viable cell count density that is at least 3-fold greater than a similar cell culture in a similar cell culture medium that contains less than 0.09±0.014 mM ornithine (or less than 0.09±0.014 mM ornithine and less than 0.2±0.03 mM putrescine).

In another embodiment, the method includes the step of adding one or more point-of-use additions to the cell culture medium. In some embodiments, the point-of-use addition is any one or more of $NaHCO_3$, glutamine, insulin, glucose, $CuSO_4$, $ZnSO_4$, $FeCl_3$, $NiSO_4$, $Na_4$ EDTA, and $Na_3$ Citrate. In one embodiment, the method employs the step of adding each of the following point-of-use chemicals to the cell culture medium: $NaHCO_3$, glutamine, insulin, glucose, $CuSO_4$, $ZnSO_4$, $FeCl_3$, $NiSO_4$, $Na_4$ EDTA, and $Na_3$ Citrate. In some embodiments, the point-of-use additions can be included in the medium at the outset.

In a specific embodiment, the aspect provides a method for cultivating cells in a serum-free medium which contains (1) ornithine at either 0.09±0.014 mM, 0.3±0.05 mM, 0.6±0.09 mM, or 0.9±0.14 mM cell culture medium; (2) optionally additionally putrescine at either 0.20±0.03 mM, 0.35±0.06, or 0.714±0.11 mM; (3) at least about 40 mM or at least about 70 mM of a mixture of amino acids including alanine, arginine, asparagine, aspartic acid, cysteine, glutamic acid, glycine, histidine, isoleucine, leucine, lysine, methionine, phenylalanine, proline, serine, threonine, tryptophan, tyrosine, and valine; (4) tocopherol and a mixture of fatty acids; (6) a mixture of nucleosides including adenosine, guanosine, cytidine, uridine, thymidine, and hypoxanthine, and (9) salts of calcium, magnesium, and phosphate, wherein the cells cultured according to this method have an average doubling time that is no more than 24 hours or at least one third the doubling time of the comparator control culture; and the cells cultured are capable of attaining a viable cell count density that is at least 15% greater or at least 3-fold greater than a similar cell culture in a similar cell culture medium that contains less than 0.09±0.015 mM ornithine (or less than 0.09±0.014 mM ornithine and less than 0.2±0.03 mM putrescine). In another embodiment, the cell culture is capable of attaining a viable cell count density that is at least 3-fold greater than a similar cell culture in a similar cell culture medium that contains less than 0.09±0.014 mM ornithine (or less than 0.09±0.014 mM ornithine and less than 0.2±0.03 mM putrescine). In one embodiment, the medium contains 7.5 g/L hydrolysate; and in another embodiment, free of hydrolysates.

In another aspect, the invention provides a method for producing a protein of interest by employing the steps of (1) introducing into a cell a nucleic acid sequence that encodes a protein of interest; (2) selecting a cell carrying that nucleic acid sequence; (3) culturing the selected cell in an embodiment of the serum-free cell culture medium described in the first aspect or according to any embodiment of the method described in the second aspect; and (4) expressing the protein of interest in the cell, wherein the protein of interest is secreted into the medium. In some embodiments, the cell used in the production of the protein is a mammalian cell capable of producing a biotherapeutic, such as CHO, 293, and BHK cell, or any derivatives of them. In one embodiment, the cell is a CHO cell, such as a CHO-K1 cell.

In some embodiments the protein of interest is an antigen binding protein. In some embodiments, the protein of interest is a protein that has an Fc domain. In some cases, those two proteins of interest may overlap, such as in the case of a receptor-Fc-fusion protein, an antibody, and a ScFv protein for example. Thus, in some embodiments, the protein of interest is an antibody, such as a human antibody or a humanized antibody, an antibody fragment, such as an Fab or F(ab')$_2$, a bispecific antibody, a trap molecule, such as a VEGF-Trap or an IL-1-Trap, an ScFv molecule, a soluble TCR-Fc fusion protein, or the like.

In one embodiment, the protein of interest is capable of being produced at an average seven day titer that is at least 7% greater, at least 14% greater, at least 80% greater, at least two fold greater, or at least three fold greater than the average seven day titer produced by a similar cell in a serum-free cell culture medium that contains less than 0.09±0.014 mM ornithine (or less than 0.09±0.014 mM ornithine and less than 0.2±0.03 mM putrescine) ("non-OS" media).

In a specific embodiment, the protein of interest is produced by (1) introducing into a CHO cell a nucleic acid sequence that encodes a protein of interest, such as an antibody or other antigen-binding protein; (2) selecting a cell carrying that nucleic acid sequence; (3) culturing the selected cell in a serum-free cell culture medium which contains (a) ornithine at either 0.09±0.014, 0.3±0.05 mM, 0.6±0.09 mM, or 0.9±0.14 mM; (b) optionally additionally putrescine at either 0.20±0.03 mM, 0.35±0.06, or 0.714±0.11 mM; (c) at least 40 mM or at least 70 mM of a mixture of amino acids including: alanine, arginine, asparagine, aspartic acid, cysteine, glutamic acid, glycine, histidine, isoleucine, leucine, lysine, methionine, phenylalanine, proline, serine, threonine, tryptophan, tyrosine, and valine; (d) tocopherol and a mixture of fatty acids; (e) a mixture of nucleosides including adenosine, guanosine, cytidine, uridine, thymidine, and hypoxanthine, and (f) salts of calcium, magnesium, and phosphate; and (d) expressing the protein of interest in the CHO cell, wherein the protein of interest is secreted into the medium. In some embodiments, the serum-free cell culture medium may include 7.5 g/L hydrolysates; or in other embodiments no hydrolysates at all.

DETAILED DESCRIPTION

The applicants have made the surprising discovery that the addition of ornithine, or a combination of ornithine and putrescine ("OS medium") improves viable cell density, cell doubling time, and protein production by a cell in a cell culture relative to a serum-free medium that contains very little or no ornithine or little or none of a combination of ornithine and putrescine ("non-OS medium").

Before the present cell cultures and methods are described, it is to be understood that this invention is not limited to particular methods and experimental conditions described, as such methods and conditions may vary. It is also to be understood that the terminology used herein is for the purpose of describing particular embodiments only, and is not intended to be limiting.

Unless defined otherwise, all technical and scientific terms used in this application have the same meaning as commonly understood by one of ordinary skill in the art to which this invention belongs. Although any methods and materials similar or equivalent to those described in this application can be used in the practice or testing of the present invention, certain specific methods and materials are now described. Units, prefixes, and symbols may be denoted in their SI accepted form. Numeric ranges recited herein are open-bracketed, meaning that they include the numbers defining the range. Unless otherwise noted, the terms "a" or "an" are to be construed as meaning "at least one of". The section headings used herein are for organizational purposes only and are not to be construed as limiting the subject matter described. The methods and techniques described herein are generally performed according to conventional methods known in the art and as described in various general and more specific references that are cited and discussed throughout the present specification unless otherwise indicated. See, e.g., Sambrook et al., Molecular Cloning: A Laboratory Manual, 3$^{rd}$ ed., Cold Spring Harbor Laboratory Press, Cold Spring Harbor, N. Y. (2001) and Ausubel et al., Current Protocols in Molecular Biology, Greene Publishing Associates (1992), Harlow and Lane Antibodies: A Laboratory Manual, Cold Spring Harbor Laboratory Press, Cold Spring Harbor, N.Y. (1990), and Julio E. Celis, Cell Biology: A Laboratory Handbook, 2$^{nd}$ ed., Academic Press, New York, N.Y. (1998), and Dieffenbach and Dveksler, PCR Primer: A Laboratory Manual, Cold Spring Harbor Laboratory Press, Cold Spring Harbor, N.Y. (1995). All publications mentioned throughout this disclosure are incorporated herein by reference in their entirety.

Definitions

As used herein "peptide," "polypeptide" and "protein" are used interchangeably throughout and refer to a molecule comprising two or more amino acid residues joined to each other by a peptide bond. Peptides, polypeptides and proteins may also include modifications such as glycosylation, lipid attachment, sulfation, gamma-carboxylation of glutamic acid residues, alkylation, hydroxylation and ADP-ribosylation. Peptides, polypeptides, and proteins can be of scientific or commercial interest, including protein-based drugs. Peptides, polypeptides, and proteins include, among other things, antibodies and chimeric or fusion proteins. Peptides, polypeptides, and proteins are produced by recombinant animal cell lines using cell culture methods.

The term "heterologous polynucleotide sequence", as used herein refers to nucleic acid polymers encoding proteins of interest, such as chimeric proteins (like trap molecules), antibodies or antibody portions (e.g., VH, VL, CDR3) that are produced as a biopharmaceutical drug substance. The heterologous polynucleotide sequence may be manufactured by genetic engineering techniques (e.g., such as a sequence encoding a chimeric protein, or a codon-optimized sequence, an intronless sequence, et cetera) and introduced into the cell, where it may reside as an episome or be intergrated into the genome of the cell. The heterologous polynucleotide sequence may be a naturally occurring sequence that is introduced into an ectopic site within the production cell genome. The heterologous polypeptide sequence may be a naturally occurring sequence from another organism, such as a sequence encoding a human ortholog.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in US Patent Application Publication No. 2010/0331527, which is incorporated by reference into this application.

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et al. (1993) PNAS USA 90:6444-6448; Poljak et al. (1994) Structure 2:1121-1123).

Still further, an antibody or antigen-binding portion thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) Human Antibodies and Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab')2 fragments, can be prepared from whole antibodies using conventional techniques, such as via papain or pepsin digestion of whole antibodies. Moreover, antibodies, antibody portions and immunoadhesion molecules can be obtained using standard recombinant DNA techniques commonly known in the art (see Sambrook et al., 1989).

The term "human antibody" is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et al., Proc. Natl. Acad. ScL USA 88: 10535, 1991; Byrn et al., Nature 344:677, 1990; and Hollenbaugh et al., "Construction of Immunoglobulin Fusion Proteins", in Current Protocols in Immunology, Suppl. 4, pages 10.19.1-10.19.11, 1992. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to a one or more ligand(s). For example, an Fc-fusion protein is a trap, such as for example an IL-1 trap (e.g., rilonacept, which contains the IL-1RAcP ligand binding region fused to the IL-1R1 extracellular region fused to Fc of hIgG1; see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

Media

The present invention provides a serum-free medium that is useful in culturing cells and producing a biopharmaceutical drug substance. "Serum-free" applies to a cell culture medium that does not contain animal sera, such as fetal bovine serum. The serum-free media may contain 7.5 g/L of hydrolysates, such as soy hydrolysate. The present invention also provides chemically defined media, which is not only serum-free, but also hydrolysate-free. "Hydrolysate-free" applies to cell culture media that contains no exogenous protein hydrolysates such as animal or plant protein hydrolysates such, for example peptones, tryptones and the like.

The elimination of serum and reducing or eliminating hydrolysates from cell culture media, while reducing lot-to-lot variability and enhancing downstream processing steps, unfortunately diminishes cell growth, viability and protein expression. Thus, chemically defined serum-free and low to no hydrolysate media requires additional ingredients to improve cell growth and protein production. The cell culture media of the invention may be supplemented with additional ingredients such as polyamines or increased concentrations of components like amino acids, salts, sugars, vitamins, hormones, growth factors, buffers, antibiotics, lipids, trace elements and the like, depending on the requirements of the cells to be cultured or the desired cell culture parameters. Specifically, the cell culture medium here is supplemented with ornithine, putrescine, or both ("OS media") to improve cell growth, cell viability, and recombinant protein production.

In some embodiments, the OS medium contains ornithine at a concentration (expressed in micromoles per liter) of at least about 90, 100, 150, 200, 250, 300, 350, 400, 450, 500, 540, 545, 550, 555, 560, 565, 568, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 620, 625, 630, 635, 640, 645, 650, 700, 750, 800, 850, or 900 µM.

In some embodiments, the media contains ornithine at a concentration of about 85, 90, 95, 100, 105, 110, 113, or 115 µM. In one embodiment, the medium contains 100 µM±15 µM ornithine. In one embodiment, the medium contains 15 mg/L±2.25 mg/L ornithine•HCl.

In some embodiments, the media contains ornithine at a concentration of about 255, 260, 265, 270, 275, 280, 285, 290, 295, 300, 305, 310, 315, 320, 325, 330, 335, 340, or 345 µM. In one embodiment, the medium contains 300 µM±45 µM ornithine. In one embodiment, the medium contains 50 mg/L±7.5 mg/L ornithine•HCl.

In some embodiments, the media contains ornithine at a concentration of about 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, or 690 µM. In one embodiment, the medium contains 600 µM±90 µM ornithine. In one embodiment, the medium contains 100 mg/L±15 mg/L ornithine•HCl.

In some embodiments, the media contains ornithine at a concentration of 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1,000, 1,005, 1,010, 1,015, 1,020, 1,025, 1,030, or 1,035 µM. In one embodiment, the medium contains 900 µM±135 µM ornithine. In one embodiment, the medium contains 150 mg/L±22.5 mg/L ornithine•HCl.

Putrescine may optionally be added to the ornithine supplemented media. Putrescine has been included, at very low concentrations, as a component in some cell culture media formulations; see for example WO 2005/028626, which describes 0.02-0.08 mg/L putrescine; U.S. Pat. No. 5,426,699 (0.08 mg/L); U.S. Pat. No. RE30,985 (0.16 mg/L); U.S. Pat. No. 5,811,299 (0.27 mg/L); U.S. Pat. No. 5,122,469 (0.5635 mg/L); U.S. Pat. No. 5,063,157 (1 mg/l); WO 2008/154014 (~100 µM-~1000 µM); US Pat. App. No. 2007/0212770 (0.5-30 mg/L polyamine; 2 mg/L putrescine; 2 mg/L putrescine+2 mg/L ornithine; 2 mg/L putrescine+10 mg/L ornithine).

In some embodiments, the media contains a combination of ornithine and putrescine, wherein the putrescine can be at a concentration of at least about 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 260, 365, 370, 375, 380, 385, 390, 395, 400, 405, or 410 µM.

In some embodiments, the media contains putrescine at a concentration of about 170, 175, 180, 185, 190, 195, 200, 205, 210, 215, 220, 225, or 230 µM. In one embodiment, the medium contains 200 µM±30 µM putrescine in addition to ≥90 µM±14 µM ornithine. In one embodiment, the medium contains 30 mg/L±4.5 mg/L putrescine•2HCl in addition to ≥15 mg/L±2.25 mg/L ornithine•HCl.

In some embodiments, the media contains putrescine at a concentration of about 295, 300, 305, 310, 315, 320, 325, 330, 335, 340, 345, 350, 355, 360, 365, 370, 375, 380, 385, 390, 395, 400, or 405 µM. In one embodiment, the medium contains 350 µM±52.5 µM putrescine in addition to ≥90 µM±14 µM ornithine. In one embodiment, the medium contains 57 mg/L±8.55 mg/L putrescine•2HCl in addition to ≥15 mg/L±2.25 mg/L ornithine•HCl.

In some embodiments, the media contains putrescine at a concentration of about 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, or 805 µM. In one embodiment, the medium contains 714 µM±105 µM putrescine in addition to ≥90 µM±14 µM ornithine. In one embodiment, the medium contains 115 mg/L±17.25 mg/L putrescine•2HCl in addition to ≥15 mg/L±2.25 mg/L ornithine•HCl.

In some embodiments, the media contains a pair-wise combination of any concentration of putrescine and ornithine listed above. In some embodiments, the media contains any pair-wise combination of about 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, or 805 µM putrescine, and about 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, or 690 µM ornithine. For example, the media in one embodiment contains about 700 µM putrescine plus any one of 510, 511, 512 µM, et sequens ornithine; or 701 µM putrescine plus any one of 510, 511, 512 µM, et sequens ornithine; et cetera. Also for example, the media in one embodiment contains about 600 µM ornithine plus any one of 700, 701, 702 µM, et sequens putrescine; or 601 µM ornithine plus any one of 700, 701, 702 µM, et sequens putrescine; et cetera. In some embodiments, the media contains 702 µM±106 µM purescine+593 µM±89 µM ornithine. In one particular embodiment, the media contains about 714 µM putrescine and 593 µM ornithine. In one embodiment, the media contains 115 mg/L±17 mg/L putrescine•2HCl and 100 mg/L±15 mg/L ornithine•HCl. In one particular embodiment, the media contains 115 mg/L putrescine•2HCl and 100 mg/L ornithine•HCl.

In one embodiment and in addition to the inclusion of ornithine or putrescine, the media contains a mixture of nucleosides in a cumulative concentration of at least 50 µM, at least 60 µM, at least 70 µM, at least 80 µM, at least 90 µM, at least 100 µM, at least 110 µM, at least 115 µM, at least 120 µM, at least 125 µM, at least 130 µM, at least 135 µM, at least 140 µM, at least 145 µM, at least 150 µM, at least 155 µM, at least 160 µM, at least 165 µM, or at least 170 µM. In one embodiment, the media contains about 174 µM±26 µM nucleoside. In one embodiment, the media contains purine derivatives in a cumulative concentration of at least 40 µM, at least 45 µM, at least 50 µM, at least 55 µM, at least 60 µM, at least 65 µM, at least 70 µM, at least 75 µM, at least 80 µM, at least 85 µM, at least 90 µM, at least 95 µM, at least 100 µM, or at least 105 µM. In one embodiment, the media contains about 106 µM±5 µM of purine derivatives. Purine derivatives include hypoxanthine and the nucleosides adenosine and guanosine. In one embodiment, the media contains pyrimidine derivatives in a cumulative concentration of at least 30 μM, at least 35 μM, at least 40 μM, at least 45 μM, at least 50 μM, at least 55 μM, at least 60 μM, or at least 65 μM. In one embodiment, the media contains about 68 μM±5 μM of pyrimidine derivatives. Pyrimidine derivatives include the nucleosides thymidine, uridine, and cytidine. In one particular embodiment, the media contains adenosine, guanosine, cytidine, uridine, thymidine and hypoxanthine.

In addition to the inclusion of ornithine or putrescine, in one embodiment, the media also contains amino acids in a cumulative concentration of at least 40 mM, wherein the amount of glutamine is not included in the calculation of the cumulative total. In one embodiment, glutamine is not included in the media, but may be supplied as a "point-of-use addition" to the media during the culturing of cells such as during the production of protein. Thus, in some embodiments, such as in the method to culture cells or the method to produce a protein of interest, the media may be supplemented with glutamine as a point-of-use addition. In one such embodiment, glutamine is added in an amount less than about 40 mM, less than about 35 mM, less than about 30 mM, less than about 25 mM, less than about 20 mM, less than about 15 mM, less than about 10 mM, less than about 8 mM, less than about 7 mM, less than about 6 mM, less than about 5 mM, less than about 4 mM, less than about 3 mM, or less than about 2.5 mM. In one embodiment the amount of glutamine in the media that was supplemented with glutamine is about 2 mM±0.5 mM.

In one embodiment, in addition to the inclusion of ornithine or a combination of both ornithine and putrescine, the media also contains amino acids having a non-polar side group in a concentration of at least 15 mM, at least 24 mM, at least 25 mM, at least 26 mM, at least 27 mM, at least 28 mM, at least 29 mM, or at least 30 mM. In one embodiment, the media contains about 30 mM of amino acids having a non-polar side group. In one embodiment, of the total amount of amino acids by mole contained within the media, at least 32%, at least 33%, at least 34%, at least 35%, at least 36%, at least 37%, at least 38%, at least 39%, at least 40%, or at least 41% are amino acids having non-polar side groups. In one embodiment, about 42%±1% by mole of the amino acids in the media are amino acids having a non-polar side group. Amino acids having a non-polar side group include alanine, valine, leucine, isoleucine, proline, phenylalanine, tryptophan, and methionine.

In one embodiment, in addition to the inclusion of ornithine or a combination of both ornithine and putrescine, the media also contains amino acids having an uncharged polar side group in a concentration of about 10 mM to 34 mM, about 11 mM to 33 mM, about 12 mM to 32 mM, about 13 mM to 31 mM, about 14 mM to 30 mM, about 15 mM to 29 mM, about 16 mM to 28 mM, about 17 mM to 27 mM, about 18 mM to 26 mM, about 19 mM to 25 mM, about 20 mM to 24 mM, about 21 mM to 23 mM, or about 22 mM. In one embodiment, the medium contains about 22 mM of amino acids having an uncharged polar side group. In another embodiment, the medium contains about 12 mM amino acids having an uncharged polar side group. In one embodiment, of the total amount by mole of amino acids contained within the media, about 14% to 46%, about 15% to 45%, about 16% to 44%, about 17% to 43%, about 18% to 42%, about 19% to 41%, about 20% to 40%, about 21% to 39%, about 22% to 38%, about 23% to 37%, about 24% to 36%, about 25% to 35%, about 26% to 34%, about 27% to 33%, about 28% to 32%, about 29% to 31%, or about 30% are amino acids having uncharged polar side groups. In one embodiment, about 30%±3% by mole of the amino acids in the media are amino acids having an uncharged polar side group. Amino acids having an uncharged polar side group include glycine, serine, threonine, cysteine, tyrosine, asparagine, and glutamine.

In one embodiment, in addition to the inclusion of ornithine or a combination of both ornithine and putrescine, the media also contains amino acids having a negative charge at pH 6 (i.e., acidic amino acids) in a concentration of about 4 mM to 14 mM, about 5 mM to 13 mM, about 6 mM to 12 mM, about 7 mM to 11 mM, about 8 mM to 10 mM, about 9 mM, or about 4 mM. In one embodiment, the media contains about 9 mM of acidic amino acids. In one embodiment, the media contains 9 mM±1 mM of acidic amino acids. In one embodiment, of the total amount by mole of amino acids contained within the media, about 8% to 18%, about 9% to 17%, about 10% to 16%, about 11% to 15%, about 12% to 14%, or about 13% are acidic amino acids. In one embodiment, about 12.6%±1% by mole of the amino acids in the media are acidic amino acids. Acidic amino acids include aspartic acid and glutamic acid.

In one embodiment, in addition to the inclusion of ornithine or a combination of both ornithine and putrescine, the media also contains amino acids having a positive charge at pH 6 (i.e., basic amino acids) in a concentration of at least 3.5 mM, at least 4 mM, at least 5 mM, at least 6 mM, at least 7 mM, at least 8 mM, at least 9 mM, at least 10 mM, or at least 11 mM. In one embodiment, the media contains about 11 mM of basic amino acids. In one embodiment, the media contains about 11.42 mM±1 mM of basic amino acids. In one embodiment, of the total amount by mole of amino acids contained within the media, at least 5%, at least 6%, at least 7%, at least 8%, at least 9%, at least 10%, at least 11%, at least 12%, at least 13%, at least 14%, or at least 15% are basic amino acids. In one embodiment, about 16% by mole of the amino acids in the media are basic amino acids. In one embodiment, about 15.8%±2.4% by mole of the amino acids in the media are basic amino acids. In one embodiment, about 21%±3.2% by mole of the amino acids in the media are basic amino acids. Basic amino acids include lysine, arginine, and histidine.

In one embodiment, in addition to the inclusion of ornithine or a combination of both ornithine and putrescine, the media also contains about 30 mM non-polar amino acids, about 22 mM uncharged polar amino acids, about 9 mM acidic amino acids, and about 11 mM basic amino acids. In one embodiment, of the amino acids in the media about 42% by mole are non-polar amino acids, about 30% by mole are uncharged polar amino acids, about 13% by mole are acidic amino acids, and about 16% by mole are basic amino acids.

In addition to the inclusion of ornithine or a combination of both ornithine and putrescine, in one embodiment, the media contains micromolar amounts of fatty acids (or fatty acid derivatives) and tocopherol. In one embodiment, the fatty acids include any one or more of linoleic acid, linolenic acid, thioctic acid, oleic acid, palmitic acid, stearic acid, arachidic acid, arachidonic acid, lauric acid, behenic acid, decanoic acid, dodecanoic acid, hexanoic acid, lignoceric acid, myristic acid, and octanoic acid. In one embodiment, the media contains tocopherol, linoleic acid, and thioctic acid.

In one embodiment, the media also contains a mixture of vitamins, which includes other nutrients and essential nutrients, at a cumulative concentration of at least about 700 μM or at least about 2 mM. In one embodiment, the mixture of vitamins contains one or more of D-biotin, choline chloride, folic acid, myo-inositol, niacinamide, pyridoxine HCl, D-pantothenic acid (hemiCa), riboflavin, thiamine HCl, vitamin B12, and the like. In one embodiment, the mixture of vitamins includes all of D-biotin, choline chloride, folic acid, myo-inositol, niacinamide, pyridoxine HCl, D-pantothenic acid (hemiCa), riboflavin, thiamine HCl, and vitamin B12.

Various embodiments of the media of the invention include any of the combinations of the above described embodiments, including chemically defined, hydrolysate-free serum-free media comprising ornithine or putrescine in the indicated amounts, plus inter alia (a) amino acids; (b) optionally nucleosides; (c) salts of divalent cations; (d) fatty acids and tocopherol; and (e) vitamins. In some embodiments, all small amounts of hydrolysates may be added to the OS media.

The applicants envision that in the practice of this invention any one or more of a variety of base media or combinations thereof, to which the ornithine or a combination of both ornithine and putrescine are added, may be used. Base media are generally known in the art and include inter alia Eagle's MEME (minimal essential media) (Eagle, Science, 1955, 112(3168):501-504), Ham's F12 (Ham, Proc. Nat'l. Acad. Sci. USA, 1965, 53:288-293), F-12 K medium, Dulbecco's medium, Dulbecco's Modified Eagle Medium (Proc. Natl. Acad. Sci. USA., 1952 August; 38(8): 747-752), DMEM/Ham's F12 1:1, Trowell's T8, A2 media Holmes and Wolf, Biophys. Biochem. Cytol., 1961, 10:389-401), Waymouth media (Davidson and Waymouth, Biochem. J., 1945, 39(2):188-199), Williams E media (William's et al., Exp. Cell Res., 1971, 69:105 et seq.), RPMI 1640 (Moore et al., J. Amer. Med. Assoc., 1967, 199:519-524), MCDB 104/110 media (Bettger et al., Proc. Nat'l. Acad. Sci. USA, 1981, 78(9):5588-5592), Ventrex HL-1 media, albumin-globulin media (Orr et al., Appl. Microbiol., 1973, 25(1): 49-54), RPMI-1640 Medium, RPMI-1641 Medium, Iscove's Modified Dulbecco's Medium, McCoys 5 A Medium, Leibovitz's L-15 Medium, and serum-free media such as EX-CELL™ 300 Series (JRH Biosciences, Lenexa, Kans.), protamine-zinc-insulin media (Weiss et al., 1974, U.S. Pat. No. 4,072,565), biotin-folate media (Cartaya, 1978, U.S. Re 30,985), Transferrin-fatty acid media (Baker, 1982, U.S. Pat. No. 4,560,655), transferrin-EGF media (Hasegawa, 1982, U.S. Pat. No. 4,615,977; Chessebeuf, 1984, U.S. Pat. No. 4,786,599), and other media permutations (see Inlow, U.S. Pat. No. 6,048,728; Drapeau, U.S. Pat. No. 7,294,484; Mather, U.S. Pat. No. 5,122,469; Furukawa, U.S. Pat. No. 5,976,833; Chen, U.S. Pat. No. 6,180,401; Chen, U.S. Pat. No. 5,856,179; Etcheverry, U.S. Pat. No. 5,705,364; Etcheverry, U.S. Pat. No. 7,666,416; Ryll, U.S. Pat. No. 6,528,286; Singh, U.S. Pat. No. 6,924,124; Luan, U.S. Pat. No. 7,429,491; and the like).

In a particular embodiment, the media is chemically defined and contains in addition to the ornithine or combination of both ornithine and putrescine: $CaCl_2$ $2H_2O$; HEPES buffer; KCl; $MgSO_4$; NaCl; $Na_2HPO_4$ or other phosphate salts; pyruvate; L-alanine; L-arginine HCl; L-asparagine $H_2O$; L-aspartic acid; L-cysteine HCl $H_2O$; L-glutamic acid; Glycine; L-histidine HCl $H_2O$; L-isoleucine; L-leucine; L-lysine HCl; L-methionine; L-ornithine HCl; L-phenylalanine; L-proline; L-serine; L-threonine; L-tryptophan; L-tyrosine 2Na 2 $H_2O$; L-valine; D-biotin; choline chloride; folic acid; myo-inositol; niacinamide; pyridoxine HCl; D-pantothenic acid; riboflavin; thiamine HCl; vitamin B12; p-aminobenzoic acid; ethanolamine HCl; Pluronic F68; DL-a-tocopherol phosphate; linoleic acid; $Na_2SeO_3$; thioctic acid; and glucose; and optionally adenosine; guanosine; cytidine; uridine; thymidine; and hypoxanthine 2Na.

In one embodiment, the starting osmolarity of the media of the invention is 200-500, 250-400, 275-350, or about 300 mOsm. During growth of the cells in the media of the invention, and in particular following any feedings according to a fed batch protocol, the osmolarity of the culture may increase up to about 350, 400, 450, or as high as 500 mOsm.

In some embodiments wherein the osmolarity of the defined medium is less than about 300, the osmolarity is brought to about 300 with the addition of one or more salts in excess of the amount specified. In one embodiment, osmolarity is increased to a desired level by adding one or more of an osmolyte selected from sodium chloride, potassium chloride, a magnesium salt, a calcium salt, an amino acid salt, a salt of a fatty acid, sodium bicarbonate, sodium carbonate, potassium carbonate, a chelator that is a salt, a sugar (e.g., galactose, glucose, sucrose, fructose, fucose, etc.), and a combination thereof. In one embodiment, the osmolyte is added over and above its concentration in a component already present in the defined medium (e.g., a sugar is added over and above the concentration specified for a sugar component).

Each and every embodiment of the media described above, as well as any other serum-free media containing at least about 90 μM ornithine (or containing a combination of at least about 100 μM ornithine plus at least about 200 μM putrescine) are hereinafter referred to as ornithine supplemented ("OS") media. Conversely, media containing no ornithine (or no ornithine/putrescine combination), or media containing less than 100 μM ornithine (or media containing less than 100 μM ornithine and less than 200 μM putrescine), are hereinafter referred to as non-ornithine supplemented ("non-OS") media.

Cell Culture

The present invention provides a cell culture comprising a cell line expressing a protein of interest in an OS medium as described above. In one embodiment, the cell culture contains insulin, which can be added as a point-of-use ingredient to the media, or can be included in the media formulation. In one embodiment, the cell line comprises cells capable of producing a biotherapeutic protein. Examples of cell lines that are routinely used to produce protein biotherapeutics include inter alia primary cells, BSC cells, HeLa cells, HepG2 cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK cells, BHK-21 cells, CHO cells, CHO-K1 cells, NS-1 cells, MRC-5 cells, WI-38 cells, BHK cells, 3T3 cells, 293 cells, RK cells, Per.C6 cells and chicken embryo cells. In one embodiment, the cell line is a CHO cell line or one or more of several specific CHO cell variants optimized for large-scale protein production, e.g., CHO-K1.

"Cell culture" or "culture" means the growth and propagation of cells outside of a multicellular organism or tissue. Suitable culture conditions for mammalian cells are known in the art. See e.g. Animal cell culture: A Practical Approach, D. Rickwood, ed., Oxford University Press, New York (1992). Mammalian cells may be cultured in suspension or while attached to a solid substrate. Fluidized bed bioreactors, hollow fiber bioreactors, roller bottles, shake flasks, or stirred tank bioreactors, with or without microcarriers, and operated in a batch, fed batch, continuous, semi-continuous, or perfusion mode are available for mammalian cell culture. Cell culture media or concentrated feed media may be added to the culture continuously or at intervals during the culture. For example, a culture may be fed once per day, every other day, every three days, or may be fed when the concentration of a specific medium component, which is being monitored, falls outside a desired range.

Animal cells, such as CHO cells, may be cultured in small scale cultures, such as in 125 ml containers having about 25 ml of media, 250 ml containers having about 50 to 100 ml of media, 500 ml containers having about 100 to 200 ml of media. Alternatively, the cultures can be large scale such as for example 1000 ml containers having about 300 to 1000 ml of media, 3000 ml containers having about 500 ml to 3000 ml of media, 8000 ml containers having about 2000 ml to 8000 ml of media, and 15000 ml containers having about 4000 ml to 15000 ml of media. Cultures for manufacturing can contain 10,000 L of media or more. Large scale cell cultures, such as for clinical manufacturing of protein therapeutics, are typically maintained for days, or even weeks, while the cells produce the desired protein(s). During this time the culture can be supplemented with a concentrated feed medium containing components, such as nutrients and amino acids, which are consumed during the course of the culture. Concentrated feed medium may be based on any cell culture media formulation. Such a concentrated feed medium can contain most of the components of the cell culture medium at, for example, about 5×, 6×, 7×, 8×, 9×, 10×, 12×, 14×, 16×, 20×, 30×, 50×, 100×, 200×, 400×, 600×, 800×, or even about 1000× of their normal useful amount. Concentrated feed media are often used in fed batch culture processes.

In some embodiments, the cell culture media is supplemented with "point-of-use additions", also known as additions, point-of-use ingredients, or point-of-use chemicals, during the course of cell growth or protein production. Point-of-use additions include any one or more of a growth factor or other proteins, a buffer, an energy source, a salt, an amino acid, a metal, and a chelator. Other proteins include transferrin and albumin. Growth factors, which include cytokines and chemokines, are generally known in the art and are known to stimulate cell growth, or in some cases, cellular differentialtion. A growth factor is usually a protein (e.g., insulin), a small peptide, or a steroid hormone, such as estrogen, DHEA, testosterone, and the like. In some cases, a growth factor may be a non-natural chemical that promotes cell proliferation or protein production, such as e.g., tetrahydrofolate (THF), methotrexate, and the like. Non-limiting examples of protein and peptide growth factors include angiopoietins, bone morphogenetic proteins (BMPs), brain-derived neurotrophic factor (BDNF), epidermal growth factor (EGF), erythropoietin (EPO), fibroblast growth factor (FGF), glial cell line-derived neurotrophic factor (GDNF), granulocyte colony-stimulating factor (G-CSF), granulocyte macrophage colony-stimulating factor (GM-CSF), growth differentiation factor-9 (GDF9), hepatocyte growth factor (HGF), hepatoma-derived growth factor (HDGF), insulin, insulin-like growth factor (IGF), migration-stimulating factor, myostatin (GDF-8), nerve growth factor (NGF) and other neurotrophins, platelet-derived growth factor (PDGF), thrombopoietin (TPO), transforming growth factor alpha (TGF-α), transforming growth factor beta(TGF-β), tumor necrosis factor-alpha(TNF-α), vascular endothelial growth factor (VEGF), wnt signaling pathway agonists, placental growth factor (PlGF), fetal Bovine somatotrophin (FBS), interleukin-1 (IL-1), IL-2, IL-3, IL-4, IL-5, IL-6, IL-7, and the like. In one embodiment, the cell culture media is supplemented with the point-of-use addition growth factor insulin. In one embodiment, the concentration of insulin in the media, i.e., the amount of insulin in the cell culture media after addition, is from about 0.1 μM to 10 μM. One or more the point-of-use additions can also be included in the media formulation of some embodiments.

Buffers are generally known in the art. The invention is not restricted to any particular buffer or buffers, and any one of ordinary skill in the art can select an appropriate buffer or buffer system for use with a particular cell line producing a particular protein. In one embodiment, a point-of-use addition buffer is $NaHCO_3$. In one embodiment, the point-of-use addition buffer comprises $NaHCO_3$. In another embodiment, the buffer is HEPES.

Energy sources for use as a point-of-use addition in cell culture are also well known in the art. Without limitation, in one embodiment, the point-of-use addition energy source is glucose. Given the particular and specific requirements of a particular cell line and the protein to be produced, in one embodiment the glucose can be added to a concentration of about 1 to 20 mM in the media. In some cases, glucose can be added at high levels up to 10 g/L.

Chelators are likewise well known in the art of cell culture and protein production. Tetrasodium EDTA dehydrate and citrate are two common chelators used in the art, although other chelators may be employed in the practice of this invention. In one embodiment, a point-of-use addition chelator is tetrasodium EDTA dihydrate. In one embodiment, a point-of-use addition chelator is citrate, such as $Na_3C_6H_5O_7$.

In one embodiment, the cell culture may be supplemented with one or more point-of-use addition amino acids, such as e.g., glutamine. In one embodiment, the cell culture media is supplemented with the point-of-use addition glutamine at a final concentration of about 1 mM to 13 mM.

Other point-of-use additions include one or more of various metal salts, such as salts of iron, nickel, zinc and copper. In one embodiment, the cell culture media is supplemented with any one or more of copper sulfate, zinc sulfate, ferric chloride; and nickel sulfate.

In one embodiment, the cell culture media is supplemented with any one or more or all of the following point-of-use additions: about 29.8 mM $NaHCO_3$, about 2 mM glutamine, about 0.86 μM insulin, about 11.1 mM glucose, about 6.54 μM zinc sulfate, about 0.168 μM copper sulfate, about 75 μM ferric chloride, about 0.639 μM nickel sulfate, about 85 μM EDTA, and about 50 μM citrate.

In one embodiment, the media is supplemented at intervals during cell culture according to a fed-batch process. Fed-batch culturing is generally known in the art and employed to optimized protein production (see Y. M. Huang et al., Biotechnol Prog. 2010 September-October; 26(5): 1400-10).

Cell viability, viable cell density, and cell doubling are improved relative to cells grown in culture without ornithine or putrescine. Regarding cell viability, cells grown in OS media show a viability that is at least 10%, at least 15%, at least 20%, at least 25%, at least 30%, at least 35%, at least 40%, at least 45%, at least 50%, at least, 55%, at least 60%, at least 65%, at least 70%, at least 75%, at least 80%, at least 85%, at least 90%, at least 95%, at least 99%, at least 100%, or at least 3-fold greater than the viability of similar or identical cells grown in non-OS media.

In some embodiments, the doubling rate of viable mammalian cells in OS media is at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 35%, at least 40%, at least 45%, at least 50%, at least 55%, at least 60%, at least 70%, at least 80%, at least 90%, at least 100%, or at least 3-fold greater than the doubling rate of mammalian cells cultured in non-OS media. In some embodiments, the doubling rate of viable mammalian cells in OS media is about 10%, 11%, 12%, 13%, 14%, 15%, 16%, 17%, 18%, 19%, 20%, 21%, 22%, 23%, 24%, 25%, 26%, 27%, 28%, 29%, or 30% greater than the doubling rate of mammalian cells in non-OS media.

In some embodiments, the doubling time of actively cycling mammalian cells is less than 30 hours, less than 29 hours, less than 28 hours, less than 27 hours, less than 26 hours, less than 25 hours, less than 24 hours, less than 23 hours, less than 22 hours, less than 21 hours, less than 20 hours, less than 19 hours, or less than 18 hours in OS media. In some embodiments, the doubling time of actively growing mammalian cells is less than 28 hours in OS media. In some embodiments, the doubling time of mammalian cells is about 27±1 hours, about 26±1 hours, about 25±1 hours, about 24±1 hours, about 23±1 hours, about 22±1 hours, or about 21±1 hours in OS media. In some embodiments, the doubling time of actively cycling mammalian cells is about 24±1 hours in OS media. In some embodiments, the doubling time of actively dividing cells cultured in OS media is at least 15%, at least 16%, at least 17%, at least 18%, at least 19%, at least 20%, or at least 25% shorter than the doubling time of actively cycling cells cultured in a non-OS media.

Protein Production

In addition to chemically defined OS media and methods of culturing cells in OS media, the present invention provides methods of producing a protein, such as a therapeutically effective antibody or other biopharmaceutical drug substance, in a cell cultured in OS media.

In some embodiments, the rate of production of protein by mammalian cells cultured in OS media is at least 5%, 10%, 15%, or 20% greater than the rate of production of protein by an identical mammalian cell cultured in non-OS media. In some embodiments the rate of production of protein in cells cultured in OS media is at least 1 pg/cell/day ("PCD"), at least 2 PCD, at least 3 PCD, at least 4 PCD, at least 5 PCD, at least 6 PCD, at least 7 PCD, at least 8 PCD, at least 9 PCD, at least 10 PCD, at least 15 PCD, at least 20 PCD, at least 25 PCD, at least 30 PCD, at least 35 PCD, at least 40 PCD, at least 45 PCD, at least 50 PCD, at least 75 PCD, or at least 100 PCD.

In some embodiments the protein production yield or titer, which can be expressed in grams of protein product per liter of culture media, from cells cultured in OS media is at least 100 mg/L, at least 1 g/L, at least 1.2 g/L, at least 1.4 g/L, at least 1.6 g/L, at least 1.8 g/L, at least 2 g/L, at least 2.5 g/L, at least 3 g/L, at least, 3.5 g/L, at least 4 g/L, at least 4.5 g/L, at least 5 g/L, at least 5.5 g/L, at least 6 g/L, at least 6.5 g/L, at least 7 g/L, at least 7.5 g/L, at least 8 g/L, at least 8.5 g/L, at least 9 g/L, at least 9.5 g/L, at least 10 g/L, or at least 20 g/L.

In some embodiments, the protein product (protein of interest) is an antibody, a human antibody, a humanized antibody, a chimeric antibody, a monoclonal antibody, a multispecific antibody, a bispecific antibody, an antigen binding antibody fragment, a single chain antibody, a diabody, triabody or tetrabody, a Fab fragment or a F(ab')2 fragment, an IgD antibody, an IgE antibody, an IgM antibody, an IgG antibody, an IgG1 antibody, an IgG2 antibody, an IgG3 antibody, or an IgG4 antibody. In one embodiment, the antibody is an IgG1 antibody. In one embodiment, the antibody is an IgG2 antibody. In one embodiment, the antibody is an IgG4 antibody.

In some embodiments, the protein of interest is a recombinant protein that contains an Fc moiety and another domain, (e.g., an Fc-fusion protein). In some embodiments, an Fc-fusion protein is a receptor Fc-fusion protein, which contains one or more of one or more extracellular domain(s) of a receptor coupled to an Fc moiety. In some embodiments, the Fc moiety comprises a hinge region followed by a CH2 and CH3 domain of an IgG. In some embodiments, the receptor Fc-fusion protein contains two or more distinct receptor chains that bind to either a single ligand or multiple ligands. For example, an Fc-fusion protein is a trap, such as for example an IL-1 trap (e.g., rilonacept, which contains the IL-1RAcP ligand binding region fused to the Il-1R1 extracellular region fused to Fc of hIgG1; see U.S. Pat. No. 6,927,004, which is herein incorporated by reference in its entirety), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. Nos. 7,087,411 and 7,279,159).

The present invention is not limited to any particular type of cell for protein production. Examples of cell types suitable for protein production include mammalian cells, insect cells, avian cells, bacterial cells, and yeast cells. The cells may be stem cells or recombinant cells transformed with a vector for recombinant gene expression, or cells transfected with a virus for producing viral products. The cells may contain a recombinant heterologous polynucleotide construct that encodes a protein of interest. That construct can be an episome or it can be an element that is physically integrated into the genome of the cell. The cells may also produce a protein of interest without having that protein encoded on a heterologous polypeptide construct. In other words, the cell may naturally encode the protein of interest, such as a B-cell producing an antibody. The cells may also be primary cells, such as chicken embryo cells, or primary cell lines. Examples of useful cells include BSC cells, LLC-MK cells, CV-1 cells, COS cells, VERO cells, MDBK cells, MDCK cells, CRFK cells, RAF cells, RK cells, TCMK-1 cells, LLCPK cells, PK15 cells, LLC-RK cells, MDOK cells, BHK-21 cells, chicken embryo cells, NS-1 cells, MRC-5 cells, WI-38 cells, BHK cells, 293 cells, RK cells, Per.C6 cells and CHO cells. In various embodiments, the cell line is a CHO cell derivative, such as CHO-K1, CHO DUX B-11, CHO DG-44, Veggie-CHO, GS-CHO, S—CHO, or CHO lec mutant lines.

In one embodiment, the cell, which is a CHO cell, ectopically expresses a protein. In one embodiment, the protein comprises an immunoglobulin heavy chain region, such as a CH1, CH2, or CH3 region. In one embodiment, the protein comprises a human or rodent immunoglobulin CH2 and CH3 region. In one embodiment, the protein comprises a human or rodent immunoglobulin CH1, CH2, and CH3 region. In one embodiment, the protein comprises a hinge region and a CH1, CH2, and CH3 region. In a specific embodiment, the protein comprises an immunoglobulin heavy chain variable domain. In a specific embodiment, the protein comprises an immunoglobulin light chain variable domain. In a specific embodiment, the protein comprises an immunoglobulin heavy chain variable domain and an immunoglobulin light chain variable domain. In a specific embodiment, the protein is an antibody, such as a human antibody, a rodent antibody, or a chimeric human/rodent antibody (e.g., human/mouse, human/rat, or human hamster).

A production phase can be conducted at any scale of culture, from individual flasks and shaker flasks or wave bags, to one-liter bioreactors, and to large scale industrial bioreactors. A large scale process can be conducted in a volume of about 100 liters to 20,000 liters or more. One or more of several means may be used to control protein production, such as temperature shift or chemical induction. A growth phase may occur at a higher temperature than a production phase. For example, a growth phase may occur at a first temperature of about 35° C. to 38° C., and a production phase may occur at a second temperature of about 29° C. to 37° C., optionally from about 30° C. to 36° C. or from about 30° C. to 34° C. In addition, chemical inducers of protein production, such as caffeine, butyrate, tamoxifen, estrogen, tetracycline, doxycycline, and hexamethylene bisacetamide (HMBA), may be added concurrent with, before, or after a temperature shift. If inducers are added after a temperature shift, they can be added from one hour to five days after the temperature shift, such as from one to two days after the temperature shift. Production cell cultures may be run as continuous feed culture system, as in a chemostat (see C. Altamirano et al., Biotechnol Prog. 2001 November-December; 17(6):1032-41), or according to a fed-batch process (Huang, 2010).

The invention is useful for improving protein production via cell culture processes. The cell lines used in the invention can be genetically engineered to express a polypeptide of commercial or scientific interest. Genetically engineering the cell line involves transfecting, transforming or transducing the cells with a recombinant polynucleotide molecule, or otherwise altering (e.g., by homologous recombination and gene activation or fusion of a recombinant cell with a non-recombinant cell) so as to cause the host cell to express a desired recombinant polypeptide. Methods and vectors for genetically engineering cells or cell lines to express a polypeptide of interest are well known to those of skill in the art; for example, various techniques are illustrated in Current Protocols in Molecular Biology. Ausubel et al., eds. (Wiley & Sons, New York, 1988, and quarterly updates); Sambrook et al., Molecular Cloning: A Laboratory Manual (Cold Spring Laboratory Press, 1989); Kaufman, R. J., Large Scale Mammalian Cell Culture, 1990, pp. 15-69. A wide variety of cell lines suitable for growth in culture are available from the American Type Culture Collection (Manassas, Va.) and commercial vendors. Examples of cell lines commonly used in the industry include VERO, BHK, HeLa, CVI (including Cos), MDCK, 293, 3T3, myeloma cell lines (e.g., NSO, NSI), PC12, WI38 cells, and Chinese hamster ovary (CHO) cells. CHO cells are widely used for the production of complex recombinant proteins, such as cytokines, clotting factors, and antibodies (Brasel et al. (1996), Blood 88:2004-2012; Kaufman et al. (1988), J. Biol Chem 263:6352-6362; McKinnon et al. (1991), J Mol Endocrinol 6:231-239; Wood et al. (1990), J Immunol. 145:3011-3016). The dihydrofolate reductase (DHFR)-deficient mutant cell lines (Urlaub et al. (1980), Proc Natl Acad Sci USA 77: 4216-4220), DXB1 1 and DG-44, are desirable CHO host cell lines because the efficient DHFR selectable and amplifiable gene expression system allows high level recombinant protein expression in these cells (Kaufman R J. (1990), Meth Enzymol 185:537-566). In addition, these cells are easy to manipulate as adherent or suspension cultures and exhibit relatively good genetic stability. CHO cells and the proteins recombinantly expressed by them have been extensively characterized and have been approved for use in clinical and commercial manufacturing by regulatory agencies. In some embodiments, the CHO cell lines are cell lines as described in U.S. Patent Application Publications No. 2010/0304436 A1, 2009/0162901 A1 and 2009/0137416 A1, and U.S. Pat. Nos. 7,455,988 B2, 7,435,553 B2, and 7,105,348 B2.

The present invention is not limited in scope by the specific embodiments described herein, which are intended as illustrations of individual aspects or embodiments of the invention. Functionally equivalent methods and components are within the scope of the invention. Various modifications of the invention, in addition to those described here, are apparent to those skilled in the art from the foregoing description and accompanying drawings. Such modifications fall within the scope of the invention.

The invention is based, in part, on the discovery that addition of ornithine or a combination of ornithine and putrescine to serum free cell culture media results in increased cell growth, viability and polypeptide production from a recombinantly engineered animal cell line (or natural cell) expressing a protein of interest, thereby enhancing culture robustness, improving the yield of the polypeptide of interest.

Example 1: Improved Viable Cell Culture Density

A 250 mL shake flask was inoculated from a seed culture of a recombinant antibody producing cell line derived from CHO K1. The inoculated cells were grown at 36.5° C. for seven days and fed glucose on days three and five. Cells were grown in each of two separate chemically defined (hydrolysate-free and serum-free) media. The first medium contained about 75 mM amino acids (Medium 1), the second medium contained about 40 mM amino acids (Medium 2), and both formulations contained no more than 2.5 µM (0.4 mg/L) putrescine. Another group of medium conditions was generated by adding soy hydrolysate at a concentration of 7.5 g/L to Medium 2. To each of the three control media, about 593 µM ornithine (as 100 mg/L L-ornithine•HCl), or a combination of about 593 µM ornithine (as 100 mg/L L-ornithine•HCl) and about 714 µM putrescine (as 115 mg/L putrescine•2HCl) were added. Aliquots of 3 mL culture were removed on days 3, 5, and 7 and viable cell counts were conducted using trypan blue exclusion on a BioProfile FLEX™ instrument (Nova Biomedical). At day zero, all cultures contained $0.8 \times 10^6$ viable cells per mL. For a given medium (Medium 1, Medium 2, or Medium 2+Soy), viable cell counts over a seven-day period revealed that CHO cells grown in media supplemented with ornitihine or ornithine plus putrescine had increased viable cell densities. The effect was especially pronounced in the hydrolysate free media (i.e., 2-fold to 4-fold or more increase in viable cell density) during the seven-day period. Hydrolysate free OS Medium 2 performed comparably to soy containing non-OS Medium 2 indicating that the cell growth benefit of soy hydrolysate can be replicated by ornithine replacement. Increased cell density by adding ornithine or ornithine and putrescine to Medium 2+soy was also observed. Results are presented in Table 1.

TABLE 1

AVERAGE VIABLE CELL CULTURE DENSITY ($10^6$ CELLS PER MILLILITER) AND X FOLD INCREASE OVER BASELINE*

| Supplement: | Time | Unsupplemented | Ornitihine | Ornithine + putrescine |
|---|---|---|---|---|
| Medium 1 | 3 days | 2.4/1X | 6.1/2.5X | 5.0/2.1X |
|  | 5 days | 3.4/1X | 12.6/3.7X | 12.4/3.6X |
|  | 7 days | 3.6/1X | 7.0/1.9X | 6.8/1.9X |
| Medium 2 | 3 days | 1.7/1X | 5.1/3.0X | 5.2/3.1X |
|  | 5 days | 2.0/1X | 7.6/3.8X | 8.0/4.0X |
|  | 7 days | 1.6/1X | 5.9/3.7X | 5.8/3.6X |

TABLE 1-continued

AVERAGE VIABLE CELL CULTURE DENSITY ($10^6$ CELLS PER MILLILITER) AND X FOLD INCREASE OVER BASELINE*

| Supplement: | Time | Unsupplemented | Ornithine | Ornithine + putrescine |
|---|---|---|---|---|
| Medium 2 + soy hydrolysate | 3 days | 5.2/1X | 5.4/1X | 4.7/0.9X |
| | 5 days | 7.7/1X | 9.3/1.2X | 9.3/1.2X |
| | 7 days | ND | 9.6/ND | 9.1/ND |

*Base line is unsupplemented media for a given medium formulation on a given day.

We also examined the effect of various amounts of ornithine•HCl (i.e., 50 mg/mL, 100 mg/mL, and 150 mg/mL) on viable cell density in Medium 3, which contains about 75 mM of amino acids and 0.4 mg/L putrescine HCl ("Medium 3"). A single seed train culture of a recombinant antibody producing cell line derived from CHO K1 was used to inoculate 50 mL TubeSpin® Bioreactors (TPP) at $0.4 \times 10^6$ cells/mL at a 15 mL working volume. The cells were grown in a 37° C. incubator for three days. Aliquots of 3 mL culture were removed on day 3 and viable cell counts were conducted using trypan blue exclusion on a BioProfile FLEX™ instrument (Nova Biomedical). All three levels of ornithine improved cell density on average (N=3) by slightly more than two fold. The results are depicted in Table 2.

TABLE 2

VIABLE CELL CULTURE DENSITY ($10^6$ CELLS PER MILLILITER) AND X FOLD INCREASE OVER BASELINE*

| | Control | Ornithine HCl | | |
|---|---|---|---|---|
| Concentration (mg/mL) | 0 | 50 | 100 | 150 |
| Viable cell density ($10^6$ cells/mL) | 1.3 | 3.2 | 3.1 | 3.1 |
| Fold increase over control | 1X | 2.5X | 2.4X | 2.4X |

*Base line is unsupplemented Medium 3.

Example 2: Improved Cell Culture Doubling Time

The doubling time of a recombinant antibody producing cell line derived from CHO K1 cells in logarithmic growth phase was determined under various cell culture media conditions. Seed train cultures were passaged at 36.5° C. in 250 mL shaker flasks over a period of 14 days in each of three separate media: Medium 1, Medium 2, and Medium 2 containing soy hydrolysate (Medium 2+Soy). Aliquots of 1 mL were removed from each condition on Day 0 and at the time of seed train passage (every 2 or 3 days), and viable cell counts were conducted using trypan blue exclusion on a CDV™ instrument (Nova Biomedical). Medium 1 was tested unsupplemented or supplemented with ornithine•HCl at 100 mg/L or both putrescine•2HCl at 115 mg/L and ornithine•HCl at 100 mg/L. Medium 2 with low putrescine•2HCl (0.4 mg/L) was tested unsupplemented or supplemented with ornithine•HCl at 100 mg/L or both putrescine•2HCl at 115 mg/L and ornithine•HCl at 100 mg/L. The results are depicted in Tables 3 and 4. Ornithine supplementation, either with or without putrescine, to Medium 1 was required to achieve significant growth. Supplementing hydrolysate free Medium 2 with ornithine or ornithine+putrescine decreased the cell doubling time by about 25% to 30%. Doubling times were also reduced to a lesser extent upon the addition of ornithine or ornithine+putrescine to hydrolysate containing Medium 2.

TABLE 3

CELL DOUBLING TIME (HOURS) AND APPROXIMATE PERCENT DOUBLING TIME DECREASE RELATIVE TO BASELINE* IN MEDIUM 1

| Supplement | Medium 1 | |
|---|---|---|
| *None | 75 | |
| Ornithine | 23 | 69% |
| Putrescine + ornithine | 21 | 72% |

*Baseline is unsupplemented Medium 1.

TABLE 4

CELL DOUBLING TIME (HOURS) AND APPROXIMATE PERCENT DOUBLING TIME DECREASE RELATIVE TO BASELINE* IN MEDIUM 2

| Supplement | Medium 2 | | Medium 2 + Soy | |
|---|---|---|---|---|
| *Unsupplemented | 27 | | 22.5 | |
| Ornithine | 21 | 22% | 20.5 | 8.9% |
| Putrescine + ornithine | 19.5 | 28% | 21 | 6.7% |

*Baseline is unsupplemented Medium 2.

Example 3: Improved Antibody Titers

Having established that the inclusion of ornithine or ornitihine+putrescine improves cell proliferation and viable cell density in culture, we further investigated the effect of those conditions on recombinant protein production titers. We examined the expression and secretion of recombinant IgG by a CHO-K1 derived cell line. In this experiment, the average antibody titer was determined at day seven in culture under various media formats. As above, Medium 1 with low putrescine (0.4 mg/L putrescine•2HCl), ornithine (100 mg/L ornithine•HCl), and both ornithine and putrescine (100 mg/L ornithine•HCl/115 mg/L putrescine•2HCl) were tested. Medium 2 and Medium 2+Soy with low putrescine (0.4 mg/L putrescine•2HCl), ornithine (100 mg/L ornithine•HCl), and both ornithine and putrescine (100 mg/L ornithine•HCl/115 mg/L putrescine•2HCl) were also tested. In all cases, the inclusion of ornithine or ornithine and putrescine at a level above 0.4 mg/L resulted in a significantly larger protein titer, i.e., at least about two-fold higher titers. The results are depicted in Table 5.

TABLE 5

AVERAGE SEVEN-DAY ANTIBODY TITERS AND APPROXIMATE FOLD INCREASE (X) IN TITER RELATIVE TO BASELINE*

| Supplement | Medium 1 | | Medium 2 | | Medium 2 + Soy | |
|---|---|---|---|---|---|---|
| Unsupplemented* | 0.31 g/L | 1X | 0.29 g/L | 1X | 0.54 g/L | 1X |
| Ornithine | 0.94 g/L | 3.0X | 0.65 g/L | 2.2X | 0.98 g/L | 1.8X |
| Putrescine + ornithine | 0.95 g/L | 3.1X | 0.64 g/L | 2.2X | 1.07 g/L | 2X |

*Baseline is set at titer in for unsupplemeted media of each type.

We also examined the effect of various amounts of ornithine•HCl (i.e., 50 mg/mL, 100 mg/mL, and 150 mg/mL) in Medium 3 on antibody production. A single seed train culture of a recombinant antibody producing cell line derived from CHO K1 was used to seed 50 mL TubeSpin® Bioreactors (TPP) at 0.4×10⁶ cells/mL at a 15 mL working volume. The cells were grown in a 37° C. incubator for three days. All three levels of ornithine supplementation improved antibody titer on the average (N=3) by slightly more than 50%. The results are depicted in Table 6.

TABLE 6

ANTIBODY TITERS (GRAMS PER LITER) AND X FOLD INCREASE IN TITER OVER BASELINE*

|  | Control | Ornithine HCl | | |
| --- | --- | --- | --- | --- |
| Supplement concentration (mg/mL) | 0 | 50 | 100 | 150 |
| Antibody titer (mg/mL) | 79 | 120 | 127 | 124 |
| Fold increase over control | 1X | 1.5X | 1.6X | 1.6X |

*Base line is unsupplemented Medium 3.

What is claimed is:

1. A method for cultivating a CHO K1 cell expressing aflibercept, comprising:
    (a) culturing the CHO K1 cell in a cell culture medium at a temperature of about 35° C. to 38° C. during a growth phase to form a cell culture, wherein said cell culture medium is serum-free and comprises plant hydrolysates, and is supplemented with 0.6±0.09 mM ornithine and 0.714±0.11 mM putrescine; and
    (b) culturing the cell culture in the cell culture medium at a temperature of about 29° C. to 37° C. during a production phase;
        wherein the cell culture has an increased viable cell culture density compared to an equivalent cell culture grown in a cell culture medium that is not supplemented with ornithine and putrescine.

2. The method of claim 1, wherein step (b) comprises culturing the cell culture at a temperature of about 30° C. to 34° C. during the production phase.

3. The method of claim 1, wherein the plant hydrolysates comprise less than or equal to 7.5 g/L soy hydrolysate.

4. The method of claim 1, wherein the cell culture medium comprises:
    (a) ≥40±6 mM of a mixture of amino acids or salts thereof;
    (b) one or more fatty acids;
    (c) a mixture of nucleosides; or
    (d) one or more divalent cations.

5. The method of claim 4, wherein:
    (a) the mixture of amino acids or salts thereof comprises one or more of alanine, arginine, asparagine, aspartic acid, cysteine, glutamic acid, glycine, histidine, isoleucine, leucine, lysine, methionine, phenylalanine, proline, serine, threonine, tryptophan, tyrosine or valine;
    (b) the one or more fatty acids are selected from the group consisting of linoleic acid, linoleic acid, thioctic acid, oleic acid, palmitic acid, stearic acid, arachidic acid, arachidonic acid, lauric acid, behenic acid, decanoic acid, dodecanoic acid, hexanoic acid, lignoceric acid, myristic acid and octanoic acid;
    (c) the mixture of nucleosides comprises one or more of adenosine, guanosine, cytidine, uridine, thymidine, or hypoxanthine; or
    (d) the divalent cation is $Ca^{2+}$, $Mg^{2+}$, or both.

6. The method of claim 1, wherein the method comprises a fed batch, continuous, semi-continuous or perfusion cell culture method.

* * * * *